US012629071B2

(12) United States Patent
Lee

(10) Patent No.: US 12,629,071 B2
(45) Date of Patent: May 19, 2026

(54) METHOD FOR PROVISION OF INFORMATION ON MENTAL DISORDER AND DEVICE FOR PROVISION OF INFORMATION ON MENTAL DISORDER, USING SAME

(71) Applicant: BWAVE CORPORATION, Goyang-si (KR)

(72) Inventor: Seung Hwan Lee, Goyang-si (KR)

(73) Assignee: BWAVE CORPORATION, Goyang-si (KR)

( * ) Notice: Subject to any disclaimer, the term of this patent is extended or adjusted under 35 U.S.C. 154(b) by 1020 days.

(21) Appl. No.: 17/640,663

(22) PCT Filed: Aug. 31, 2020

(86) PCT No.: PCT/KR2020/011634
§ 371 (c)(1),
(2) Date: Mar. 4, 2022

(87) PCT Pub. No.: WO2021/080157
PCT Pub. Date: Apr. 29, 2021

(65) Prior Publication Data
US 2022/0338772 A1     Oct. 27, 2022

(30) Foreign Application Priority Data
Oct. 23, 2019     (KR) ........................ 10-2019-0132374

(51) Int. Cl.
*A61B 5/16*          (2006.01)
*A61B 5/00*          (2006.01)
*A61B 5/377*         (2021.01)
*G16H 20/70*         (2018.01)

(52) U.S. Cl.
CPC .............. *A61B 5/165* (2013.01); *A61B 5/377* (2021.01); *A61B 5/7264* (2013.01); *G16H 20/70* (2018.01)

(58) Field of Classification Search
None
See application file for complete search history.

(56) References Cited

U.S. PATENT DOCUMENTS

| | | | |
|---|---|---|---|
| 2011/0119212 A1* | 5/2011 | De Bruin ............... | A61B 5/369 706/12 |
| 2012/0296569 A1* | 11/2012 | Shahaf ................... | A61B 5/383 702/19 |
| 2015/0305686 A1* | 10/2015 | Coleman .............. | A61B 5/7264 600/301 |

FOREIGN PATENT DOCUMENTS

| | | |
|---|---|---|
| KR | 10-2014-0103560 A | 8/2014 |
| KR | 10-2015-0030498 A | 3/2015 |

OTHER PUBLICATIONS

Shim et al; Machine-learning-based diagnosis of schizophrenia using combined sensor-level and source-level EEG features; Schizophrenia Research 176 (2016) 314-319 (Year: 2016).*

* cited by examiner

*Primary Examiner* — Jay B Shah
(74) *Attorney, Agent, or Firm* — INVENSTONE PATENT, LLC

(57)     ABSTRACT

The present invention relates to a method for provision of information on a mental disorder and a device utilizing same, the method for provision of information on a mental disorder being implemented by a processor, and comprising: outputting a stimulus to a subject in order to generate brain waves; receiving brain wave data and brain activity data measured in the subject during outputting the stimulus; and determining whether a mental disorder is present in the subject by using a classification model configured to classify mental disorders on the basis of the brain wave data and the brain activity data.

19 Claims, 15 Drawing Sheets

| | PTSD | | | MDD | HCs | p |
|---|---|---|---|---|---|---|
| | PTSDm | PTSDc | Total PTSD | | | |
| Cases (N) | 28 | 23 | 51 | 67 | 39 | |
| Gender (male/female) | 14 / 14 | 10 / 13 | 24 / 27 | 24 / 43 | 18 / 21 | 0.429 |
| Age (years) | 43.50±8.88 | 42.09±12.33 | 42.86±10.49 | 42.09±9.83 | 38.74±9.05 | 0.118 |
| Education (years) | 13.64±3.11 | 12.83±3.16 | 13.27±3.13 | 13.54±3.53 | 14.47±2.15 | 0.198 |
| Symptom score | | | | | | |
| BDI | 26.64±12.66 | 26.50±12.88 | 26.58±12.62 | 25.81±8.39 | | |
| BAI | 28.71±15.75 | 31.38±15.90 | 29.36±15.71 | 24.43±9.83 | | |
| IES-R | 53.38±20.59 | 55.00±20.72 | 53.21±20.80 | | | |

|  | PTSD | | | MDD | HCs | p |
|---|---|---|---|---|---|---|
|  | PTSDm | PTSDc | Total PTSD | | | |
| Amplitude | | | | | | |
| Fz | 7.62 ± 3.26 | 8.06 ± 4.46 | 7.82 ± 3.81 | 10.55 ± 4.85 | 11.03 ± 3.81 | 0.000*+ |
| Cz | 7.63 ± 3.93 | 8.08 ± 4.27 | 7.83 ± 4.05 | 10.31 ± 4.12 | 11.21 ± 3.92 | 0.000*+ |
| Pz | 6.97 ± 4.54 | 7.03 ± 3.97 | 7.12 ± 4.26 | 9.42 ± 3.54 | 10.24 ± 3.72 | 0.000*+ |
| T7 | 3.93 ± 2.28 | 4.60 ± 2.75 | 4.24 ± 2.49 | 4.95 ± 2.31 | 5.51 ± 2.05 | 0.034* |
| T8 | 4.48 ± 2.01 | 4.61 ± 2.26 | 4.54 ± 2.11 | 5.69 ± 2.30 | 6.55 ± 2.30 | 0.000*+ |
| Latency | | | | | | |
| Fz | 361.25 ± 35.30 | 360.52 ± 38.78 | 360.92 ± 36.54 | 361.11 ± 35.86 | 350.31 ± 22.17 | 0.116 |
| Cz | 364.36 ± 35.36 | 367.39 ± 43.93 | 365.73 ± 39.07 | 349.51 ± 35.74 | 355.79 ± 24.59 | 0.043+ |
| Pz | 390.11 ± 37.57 | 377.48 ± 41.21 | 384.41 ± 39.37 | 366.22 ± 35.52 | 366.00 ± 27.71 | 0.009*+ |
| T7 | 371.18 ± 50.62 | 376.35 ± 47.36 | 373.51 ± 48.76 | 365.30 ± 37.24 | 357.23 ± 33.84 | 0.17 |
| T8 | 374.43 ± 37.70 | 380.39 ± 45.67 | 377.12 ± 41.16 | 355.75 ± 40.32 | 368.59 ± 30.87 | 0.012+ |

FIG. 4C

| ROI (structure) | MNI coordination | | | Talairach coordination | | | T score |
|---|---|---|---|---|---|---|---|
| | X | Y | Z | X | Y | Z | |
| PTSD < HCs | | | | | | | |
| Anterior Cingulate | 10 | 25 | 30 | 10 | 26 | 26 | −4.11 |
| Cingulate Gyrus | 0 | −40 | 25 | 0 | −38 | 25 | −4.07 |
| Cuneus | −5 | −65 | 5 | −5 | −63 | 8 | −4.1 |
| Fusiform Gyrus | −25 | −50 | −15 | −25 | −49 | −10 | −4.07 |
| Inferior Occipital Gyrus | −25 | −90 | −20 | −25 | −88 | −12 | −4.1 |
| Inferior Temporal Gyrus | 40 | −20 | −35 | 40 | −21 | −28 | −4.08 |
| Insula | 30 | −30 | 15 | 30 | −28 | 15 | −4.11 |
| Lingual Gyrus | −10 | −55 | 0 | −10 | −53 | 3 | −4.13 |
| Medial Frontal Gyrus | −15 | 25 | 35 | −15 | 26 | 31 | −4.07 |
| Middle Occipital Gyrus | −20 | −90 | −15 | −20 | −88 | −8 | −4.4 |
| Parahippocampal Gyrus | −10 | −50 | 0 | −10 | −48 | 2 | −4.18 |
| Posterior Cingulate | −5 | −60 | 5 | −5 | −58 | 8 | −4.25 |
| Precuneus | 0 | −70 | 15 | 0 | −67 | 17 | −4.07 |
| Sub-Gyral | −15 | −45 | −10 | −15 | −44 | −6 | −4.09 |
| Superior Temporal Gyrus | 35 | −35 | 15 | 35 | −33 | 15 | −4.13 |
| Uncus | 30 | −15 | −35 | 30 | −16 | −29 | −4.11 |
| MDD < HCs | | | | | | | |
| Cuneus | −5 | −65 | 5 | −5 | −63 | 8 | −4.43 |
| Fusiform Gyrus | −20 | −60 | −15 | −20 | −59 | −10 | −4.06 |
| Lingual Gyrus | −5 | −65 | 0 | −5 | −63 | 3 | −4.06 |
| Parahippocampal Gyrus | −10 | −50 | 0 | −10 | −48 | 2 | −4.05 |
| Posterior Cingulate | −5 | −60 | 5 | −5 | −58 | 8 | −4.07 |
| PTSD < MDD | | | | | | | |
| Angular gyrus | −35 | −80 | 30 | −35 | −76 | 31 | −4.32 |
| Anterior Cingulate | 10 | 25 | 30 | 10 | 26 | 26 | −3.96 |
| Cingulate Gyrus | −20 | −45 | 25 | −20 | −42 | 25 | −3.89 |
| Cuneus | −25 | −85 | 25 | −25 | −81 | 27 | −3.91 |
| Insula | −40 | −45 | 20 | −40 | −43 | 21 | −3.9 |
| Medial Frontal Gyrus | 15 | 25 | 35 | 15 | 26 | 31 | −3.9 |
| Middle Frontal Gyrus | 20 | 20 | 45 | 20 | 21 | 40 | −4.11 |
| Middle Temporal Gyrus | −35 | −60 | 20 | −35 | −57 | 21 | −3.96 |
| Parahippocampal Gyrus | 15 | −5 | −15 | 15 | −5 | −12 | −3.93 |
| Posterior Cingulate | −5 | −40 | 25 | −5 | −38 | 25 | −3.9 |
| Precuneus | −20 | −45 | 30 | −20 | −42 | 30 | −3.91 |
| Sub-Gyral | −30 | −60 | 25 | −30 | −57 | 26 | −4.25 |
| Superior Frontal Gyrus | 20 | 15 | 50 | 20 | 17 | 45 | −3.95 |
| Superior Occipital Gyrus | −30 | −85 | 25 | −30 | −81 | 27 | −3.94 |
| Superior Temporal Gyrus | −35 | −55 | 20 | −35 | −52 | 21 | −3.91 |
| Transverse Temporal Gyrus | −35 | −35 | 10 | −35 | −33 | 11 | −4.09 |
| PTSDc < MDD | | | | | | | |
| Anterior Cingulate | −10 | 25 | 30 | −10 | 26 | 26 | −4.42 |
| Cingulate Gyrus | −15 | 10 | 40 | −15 | 12 | 36 | −4.28 |
| Inferior frontal gyrus | 35 | 5 | 30 | 35 | 6 | 27 | −4.36 |
| Medial Frontal Gyrus | −15 | 25 | 35 | −15 | 26 | 31 | −4.29 |
| Superior Temporal Gyrus | −35 | −55 | 25 | −35 | −52 | 26 | −4.28 |

FIG. 5B

PTSD vs. HCs

MDD vs. HCs (b). Source-level feature

PTSDm vs. MDD (a). Sensor-level feature

| Classification pair | Sensor | | | Source | | | Sensor + source | | |
|---|---|---|---|---|---|---|---|---|---|
| | Accuracy | Specificity | Sensitivity | Accuracy | Specificity | Sensitivity | Accuracy | Specificity | Sensitivity |
| MDD vs. HCs | 63.21 | 41.03 | 71.64 | 67.92 | 89.55 | 30.77 | 66.04 | 97.01 | 12.82 |
| PTSD vs. HCs | 67.78 | 68.63 | 66.67 | 80 | 86.27 | 71.79 | 75.56 | 88.24 | 58.97 |
| PTSD vs. MDD | 66.1 | 71.64 | 58.82 | 70.34 | 74.51 | 67.16 | 66.1 | 78.43 | 56.72 |
| PTSDm vs. HCs | 71.64 | 76.92 | 64.29 | 82.09 | 85.71 | 79.49 | 79.1 | 67.86 | 87.18 |
| PTSDm vs. MDD | 70.53 | 86.57 | 13.04 | 70.53 | 0 | 100 | 71.58 | 50 | 80.6 |
| PTSDc vs. HCs | 77.42 | 60.87 | 87.18 | 82.26 | 73.91 | 87.18 | 72.58 | 56.22 | 82.05 |
| PTSDc vs. MDD | 74.44 | 88.06 | 26.09 | 75.56 | 34.78 | 89.55 | 76.67 | 34.78 | 91.04 |

FIG. 7

METHOD FOR PROVISION OF INFORMATION ON MENTAL DISORDER AND DEVICE FOR PROVISION OF INFORMATION ON MENTAL DISORDER, USING SAME

CROSS-REFERENCE TO RELATED APPLICATIONS

This application is a national stage of International Application No. PCT/KR2020/011634, filed on Aug. 31, 2020, which claims the benefit of priority to Korean Application No. 10-2019-0132374, filed on Oct. 23, 2019 in the Korean Intellectual Property Office, the disclosures of which are incorporated herein by reference.

TECHNICAL FIELD

The present invention relates to a method for provision of information on a mental disorder and a device for provision of information on a mental disorder using the same, and more particularly, to a method for provision of information on a mental disorder which provides information whether a mental disorder occurs on the basis of brain wave data and a device for provision of information on a mental disorder using the same.

BACKGROUND

A mental disorder may refer to a dysfunction in psychology or behaviors. At this time, the mental disorder may be caused by genetic causes, physical and organic causes, and mental and psychological causes such as a stress.

In the modern society, as the frequency of exposure to psychological stress increases, the incidence of the mental diseases such as a major depressive disorder (MDD) caused by the stress and a post-traumatic stress disorder (PTSD) in which the stress leads to a traumatic state is also increased.

For example, the post-traumatic stress disorder (PTSD) is a disease in which symptoms such as re-experience of trauma, avoidance of trauma-related stimuli, and an arousal reaction of increased paralysis of general reaction appearing after exposure to extremely traumatic events such as war, assault, kidnapping, hostage, and accident.

Recently, it has been reported that catastrophic events frequently occur and the post-traumatic stress disorder occurs in people who have directly or indirectly experienced these events. Specifically, people with occupations such as firefighters or police are not only exposed to general stress, but also have to face many incidents and accidents due to their occupational characteristics so that they may be more likely to be exposed to the post-traumatic stress disorder.

Such a post-traumatic stress disorder develops a complication with another mental disorder such as depression so that it is very important to accurately diagnose the post-traumatic stress disorder.

However, certain mental disorders such as the post-traumatic stress disorder or the major depressive disorder have many similar symptoms which are shared and vary in severity between individuals, which makes it difficult to accurately distinguish between them.

As described above, the development of optical classification criteria for specific mental disorders which share similar symptoms may be important to accurately diagnose the mental disorders.

Accordingly, development for new diagnostic criteria and a system of mental disorders which may improve the accuracy of the diagnosis is consistently demanded.

DETAILED DESCRIPTION

In the meantime, in order to clearly diagnose the mental disorders which share the similar symptoms, a functional magnetic resonance imaging (fMRI) on the basis of a dynamic neural activity which represents a unique characteristic of each disorder has emerged.

To be more specific, according to the fMRI analysis, a patient with a post-traumatic stress disorder and a patient with a major depressive disorder may have different neural responses when reading emotional texts. Therefore, the fMRI analysis result may be provided as information on accurate diagnosis of a mental disorder.

In the meantime, in the case of the fMRI, the patients may complain of anxiety or fear during the diagnosis process. Moreover, when the fMRI is applied to the diagnosis of mental disorders, the fMRI still has many limitations such as expensive analysis costs, spatial and temporal restrictions.

Specifically, fMRI focuses only on the neural activity during processing the emotional information, but does not consider important pathologies such as an altered cognitive process so that there may be limitations in providing reliable information for accurate diagnosis of the mental disorder.

In the meantime, the inventors of the invention have paid attention that with respect to the mental disorder, changes in biosignals will precede as a part of the human body's response.

Specifically, the inventors of the present invention have paid attention to the change in brain wave data related to the incidence of the mental disorder and have recognized that the above-described limitations of the fMRI analysis can be overcome using the brain wave data.

To be more specific, the inventors of the present invention have recognized that event-related potentials (ERPs) which are brain wave signals represented through specific events (a visual stimulus or an auditory stimulus) reflects the change in the cognitive process so that the mental disorders having similar symptoms may be classified with a higher reliability.

As a result, the inventors of the present invention could develop a system for provision of information on a mental disorder on the basis of a brain wave signal generated from a specific stimulus.

In the meantime, the inventors of the present invention could recognize that the application of not only brain wave data according to the specific stimulus which may be acquired from a sensor of the brain wave signal, but also brain activity data of a source activity which is activated during outputting the stimulus can contribute to the accurate diagnosis of the mental disorder.

Specifically, the inventors of the present invention may apply the brain activity data to the information provision system together with the brain wave data, by considering that the brain activity data reflects a functional neurological measurement value.

Moreover, the inventors of the present invention may apply a classification model which is trained by the brain wave data and the brain activity data to predict the mental disorder having a higher incidence risk to the information provision system in order to provide information with a high reliability.

Specifically, the inventors of the present invention may confirm that the classification model is applied not only to predict whether the mental disorder occurs, but also to classify specific mental disorders which share the similar symptoms, such as PTSD and the major depressive disorder with a high accuracy.

Accordingly, an object to be achieved by the present invention is to provide a method for provision of information on a mental disorder configured to determine whether a mental disorder is present in a subject using a classification model, together with brain wave data and brain activity data, acquired during outputting a stimulus.

Another object to be achieved by the present invention is to provide a device for provision of information on a mental disorder including an output unit configured to output a stimulus, a reception unit configured to receive brain wave data and brain activity data during outputting the stimulus, and a processor configured to determine whether a mental disorder is present in the subject on the basis of the brain wave data and brain activity data.

Objects of the present invention are not limited to the above-mentioned objects, and other objects, which are not mentioned above, can be clearly understood by those skilled in the art from the following descriptions.

In order to achieve the above-described objects, a method for provision of information on a mental disorder according to an exemplary embodiment of the present invention is provided. The method for provision of information according to an aspect of the present invention is performed by a processor and includes outputting a stimulus to a subject in order to generate brain waves; receiving brain wave data and brain activity data measured in the subject during outputting the stimulus; and determining whether a mental disorder is present in the subject by using a classification model configured to classify mental disorders on the basis of the brain wave data and the brain activity data.

According to a feature of the present invention, the method for provision of information according to the exemplary embodiment of the present invention may further include, before the receiving, generating brain wave activity data, on the basis of the brain wave data.

According to another feature of the present invention, the brain wave data may include latency data. At this time, wherein the generating brain activity data may include: measuring brain activity data which is defined as a source activity for a brain area which is activated during generating a stimulus and determining brain activity data corresponding to the latency.

According to still another feature of the present invention, generating brain activity data may include converting the brain wave data into the brain activity data using at least one of low-resolution brain electromagnetic tomography (LO-RETA), standardized low-resolution brain electromagnetic tomography (sLORETA), exact resolution brain electromagnetic tomography (eLORETA), minimum-norm estimate (MNE), dynamic statistical parametric mapping (dSPM), linearly constrained minimum variance (LCMV) beamformers programs—LORETA/sLORETA toolbox, Brainstrom, eConnectome, fieldtrip, and EEGlab.

According to still another feature of the present invention, the brain wave data may include amplitude data or latency data.

According to still another feature of the present invention, the amplitude data may include amplitude data in at least one standard electrode placement area of Fz, Cz, Pz, C3, T3, T4, T7, and T8 and the latency data may include latency data in the at least one standard electrode placement area.

According to still another feature of the present invention, at least one standard electrode placement area may include Fz, Cz, and Pz.

According to still another feature of the present invention, the brain activity data may include a source activity in at least one brain area of anterior cingulate, cingulate gyms, cuneus, fusiform gyms, inferior occipital gyrus, inferior temporal gyrus, insula, lingual gyms, medial frontal gyms, middle frontal gyrus, middle occipital gyrus, middle temporal gyrus, parahippocampal gyrus, posterior cingulate, precuneus, sub-gyral, superior frontal gyms, superior occipital gyrus, superior temporal gyms, transverse temporal gyms, uncus, angular gyrus, and inferior frontal gyrus.

According to still another feature of the present invention, the classification model is a model configured to classify at least one of a post-traumatic stress disorder, a major depressive disorder, a post-traumatic stress disorder having a major depressive disorder, and the normal, on the basis of the brain wave data and the brain activity data.

According to still another feature of the present invention, the classification model may be configured to classify the post-traumatic stress disorder or the normal. At this time, the brain activity data may include a source activity in at least one area of cingulate gyrus, fusiform gyrus, inferior occipital gyms, inferior temporal gyrus, lingual gyrus, medial frontal gyms, middle occipital gyrus, parahippocampal gyms, posterior cingulate, sub-gyral, superior frontal gyrus, and superior occipital gyrus.

According to still another feature of the present invention, the classification model is configured to classify the major depressive disorder or the normal and the brain activity data may include a source activity in at least one brain area of angular gyrus, cuneus, fusiform gyms, inferior occipital gyrus, lingual gyrus, parahippocampal gyms, posterior cingulate, precuneus, and superior occipital gyrus.

According to still another feature of the present invention, the classification model is configured to classify the post-traumatic stress disorder or the major depressive disorder. At this time, wherein the brain activity data may include a source activity in at least one brain area of cingulate gyms, posterior cingulate, and sub-gyral.

According to still another feature of the present invention, wherein the outputting a stimulus may include randomly outputting a standard sound stimulus and a target sound stimulus having a different frequency or dB from the standard sound stimulus, for the subject.

According to still another feature of the present invention, the method for provision of information according to the exemplary embodiment of the present invention may further include, after the randomly outputting, receiving selection of a target sound stimulus to the subject. At this time, wherein the receiving the brain wave data may include acquiring brain wave data having a maximum value generated between 200 and 500 ms, after selecting the target sound stimulus. In order to achieve the above-described object, a device for provision of information on a mental disorder according to an exemplary embodiment of the present invention is provided. The device for provision of information according to an exemplary embodiment of the present invention includes an output unit configured to output a stimulus to a subject in order to generate brain waves; a reception unit configured to receive brain wave data and brain activity data measured in the subject during outputting the stimulus; and a processor connected to communicate with the reception unit. At this time, the processor may be configured to determine whether a mental disorder is present in the subject by using a classification model configured to classify mental disorders on the basis of the brain wave data and the brain activity data.

According to a feature of the present invention, the processor may be configured to generate brain wave activity data on the basis of the brain wave data.

According to another feature of the present invention, the brain wave data includes latency data and the processor may be configured to measure brain activity data defined as a source activity for a brain area which is activated during generating a stimulus and determine brain activity data corresponding to the latency.

According to still another feature of the present invention, the processor may be configured to convert the brain wave data into the brain activity data using at least one of low-resolution brain electromagnetic tomography (LO-RETA), standardized low-resolution brain electromagnetic tomography (sLORETA), exact resolution brain electromagnetic tomography (eLORETA), minimum-norm estimate (MNE), dynamic statistical parametric mapping (dSPM), linearly constrained minimum variance (LCMV) beamformers programs—LORETA/sLORETA toolbox, Brainstrom, eConnectome, fieldtrip, and EEGlab.

According to still another feature of the present invention, the brain wave data may include amplitude data or latency data.

According to still another feature of the present invention, the amplitude data may include amplitude data in at least one standard electrode placement area of Fz, Cz, Pz, C3, T3, T4, T7, and T8 and the latency data may include latency data in the at least one standard electrode placement area.

According to still another feature of the present invention, at least one standard electrode placement area may include Fz, Cz, and Pz.

According to still another feature of the present invention, the classification model may be a model configured to classify at least one of a post-traumatic stress disorder, a major depressive disorder, a post-traumatic stress disorder having a major depressive disorder, and the normal, on the basis of the brain wave data and the brain activity data.

Other detailed matters of the exemplary embodiments are included in the detailed description and the drawings.

Effects of the Invention

According to the present invention, the application of not only brain wave data according to the specific stimulus which may be acquired from a sensor of the brain wave signal, but also brain activity data of a source activity which is activated while outputting the stimulus can contribute to the accurate diagnosis of the mental disorder.

Therefore, the present invention may overcome the limitations of the analysis method such as fMRI that focuses only on the neural activity during processing emotional information, but does not consider important pathologies such as an altered cognitive process so that information with a low reliability is provided and still has many limitations such as accompanied expensive analysis costs and spatial and temporal restrictions.

Moreover, the present invention provides an information provision system which applies a classification model which is trained by brain wave data and brain activity data to predict a mental disorder having a higher incidence risk to provide information with a high reliability.

Specifically, the present invention can not only predict whether the mental disorder occurs, but also classify specific mental disorders which share the similar symptoms, such as PTSD and the major depressive disorder with a high accuracy.

The effects according to the present invention are not limited to the contents exemplified above, and more various effects are included in the present invention.

DESCRIPTION OF DRAWINGS

FIG. 3 illustrates evaluation data of a device for provision of information on a mental disorder according to an exemplary embodiment of the present invention.

FIGS. 4A to 4C illustrate a brain wave data analysis result depending on whether a mental disorder is present in a subject.

FIGS. 5A to 5E illustrate a brain activity data analysis result depending on whether a mental disorder is present in a subject.

FIG. 7 illustrates a mental disorder classification result on the basis of a classification model used for various exemplary embodiments of the present invention.

Figure 1A:
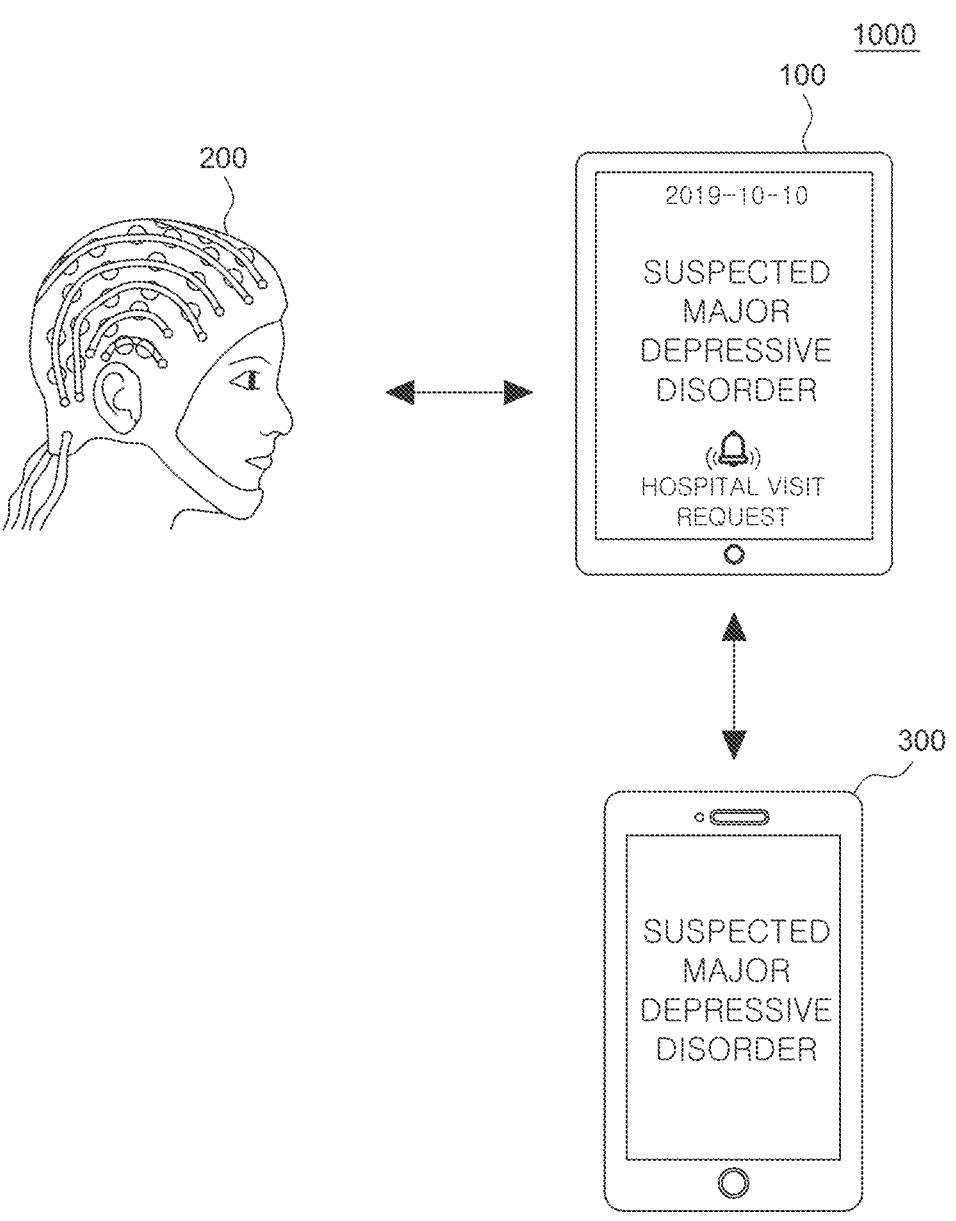
FIG. 1A is a schematic view for explaining a system for provision of information on a mental disorder using biosignal data according to an exemplary embodiment of the present invention.

Advantages and characteristics of the present invention and a method of achieving the advantages and characteristics will be clear by referring to exemplary embodiments described below in detail together with the accompanying drawings.

However, the present invention is not limited to the following exemplary embodiments but may be implemented in various different forms. The exemplary embodiments are provided only to complete the disclosure of the present invention and to fully provide a person having ordinary skill in the art to which the present invention pertains with the category of the disclosure, and the present invention will be defined by the appended claims.

Although the terms "first", "second", and the like are used for describing various components, these components are not confined by these terms. These terms are merely used for distinguishing one component from the other components. Therefore, a first component to be mentioned below may be a second component in a technical concept of the present invention.

Like reference numerals generally denote like elements throughout the specification.

The features of various embodiments of the present invention can be partially or entirely bonded to or combined with each other and can be interlocked and operated in technically various ways understood by those skilled in the art, and the embodiments can be carried out independently of or in association with each other.

For clarity of interpretation of the present specification, terms used in the present specification will be defined below.

The terminology "mental disorder" used in the present specification may refer to a dysfunction in psychology or behaviors.

In the specification of the present invention, the mental disorder may be at least one of a post-traumatic stress disorder, a major depressive disorder, and a post-traumatic stress disorder with a major depressive disorder, but, it is not limited thereto.

The terminology "stimulus" used in the present specification may refer to a stimulus inducing generation of the brain wave or the change of the brain wave.

In the specification of the present invention, the stimulus may refer to a visual stimulus and an auditory stimulus, but is not limited thereto.

Desirably, the stimulus may be an auditory stimulus. For example, an auditory stimulus configured by a standard sound stimulus of 1000 Hz and a target sound stimulus of 1500 Hz may be randomly output for the subject. At this time, the brain wave signal generated between 200 and 500 ms of the target sound stimulus output may be related to the mental disorder.

The terminology "brain wave data" used in the present specification may refer to an electroencephalogram (EEG) signal value recorded in a sensor which senses a brain wave. To be more specific, the brain wave data may be an EEG signal of a positive potential response that appears after a stimulus of a specific intensity, but it is not limited thereto.

In the meantime, the brain wave data may be a signal or a signal value acquired from a sensor so that in the present specification, the brain wave data may be interpreted as the same meaning as the sensor data.

In the meantime, the brain wave data may be at least one of amplitude data and latency data. At this time, the amplitude may be related to a quantity of a nerve source according to the stimulus and the latency may be associated with a processing speed according to the stimulus.

Desirably, the brain wave data may be p300 amplitude data or p300 latency data having a maximum value generated between 200 and 500 ms after selecting the above-described target sound stimulus of 1500 Hz, but is not limited thereto.

In the meantime, according to the characteristic of the present invention, the brain wave data may be brain wave data measured in at least one standard electrode placement area of Fz, Cz, Pz, C3, T3 (T7), and T4 (T8). For example, the brain wave data may be amplitude data in at least one standard electrode placement area of Fz, Cz, Pz, C3, T3 (T7), and T4 (T8) or latency data in at least one standard electrode placement area of Fz, Cz, Pz, C3, T3 (T7), and T4 (T8).

At this time, the brain wave data may be brain wave data acquired from the electrodes of Fz, Cz, and Pz, but is not limited thereto and may include brain wave data measured from at least two electrodes of Fp1, Fp2, F3, Fz, F4, F8, T7, C3, C4, Cz, T8, P7, P3, Pz, P4, P8, O1, O2, FCz, TP9, TP10, Oz, AFz, F7, Fpz, AF7, AF3, AF4, AFB, F9, F5, F1, F2, F6, F10, FT9, FT7, FC5, FC3, FC1, FC2, FC4, FC6, FT8, FT10, C5, C1, C2, C6, TP7, CP5, CP3, CP1, CPz, CP2, CP4, CP6, TP8, P9, P5, P1, P2, P6, P10, PO9, PO7, PO3, POz, PO4, PO8, PO10, O9, Iz, O10, F11, F12, FT11, FT12, TP11, TP12, PO11, PO12, P11, P12, I11, I12, and IIz.

In the meantime, the brain wave data may be data which is filtered in a band-pass of 1 to 30 Hz and is processed in the range of 100 ms before outputting the target sound stimulus and 900 ms after outputting the target sound stimulus, but it is not limited thereto.

The terminology "brain activity data" used in the present specification may refer to data of source activity which is activated during outputting a stimulus. At this time, the source activity may correspond to a current source density (CSD) for the brain active area.

For example, the brain activity data may include a source activity in at least one brain area of anterior cingulate, cingulate gyrus, cuneus, fusiform gyrus, inferior occipital gyrus, inferior temporal gyrus, insula, lingual gyms, medial frontal gyrus, middle frontal gyrus, middle occipital gyms, middle temporal gyms, parahippocampal gyms, posterior cingulate, precuneus, sub-gyral, superior frontal gyrus, superior occipital gyms, superior temporal gyms, transverse temporal gyms, uncus, angular gyrus, and inferior frontal gyrus.

As the brain activity data is defined as a source activity, the brain activity data may be interpreted as the same meaning as source data in the present specification.

In the meantime, the brain activity data may be generated on the basis of the above-described brain wave data.

For example, the brain activity data may be acquired by measuring brain activity data which is activated during generating the stimulus and determining brain activity data corresponding to the latency on the basis of the latency data. To be more specific, the brain activity data may be generated in a source space of a cortical gray matter having a resolution of 5 mm and 6239 voxels. At this time, when the brain wave data is P300 latency data, a time window to estimate P300 CSD may be set on the basis of an average and a standard deviation of P300 latency.

For example, the brain activity data may be brain activity data corresponding to a time window obtained by adding or subtracting twice the standard deviation to or from the average P300 latency.

Further, the brain activity data may be acquired by estimating a source activity for a voxel corresponding to the source space using at least one of low-resolution brain electromagnetic tomography (LORETA), standardized low-resolution brain electromagnetic tomography (sLORETA), exact resolution brain electromagnetic tomography (eLORETA), minimum-norm estimate (MNE), dynamic statistical parametric mapping (dSPM), linearly constrained minimum variance (LCMV) beamformers programs—LORETA/sLORETA toolbox, Brainstrom, eConnectome, fieldtrip, and EEGlab.

Desirably, the brain activity data may be data acquired by sLORETA, but is not limited thereto.

The terminology "classification model" used in the present specification may refer to a model trained to classify mental disorders, on the basis of brain wave data and brain activity data of a subject acquired from a brain wave measuring device and a brain electromagnetic tomography.

To be more specific, the classification model may be a model configured to classify at least one of a post-traumatic stress disorder, a major depressive disorder, a post-traumatic stress disorder with a major depressive disorder, and the normal, on the basis of the data.

According to the characteristic of the present invention, the classification model may be configured to classify the post-traumatic stress disorder or the normal. At this time, the classification model may be a model trained to classify the post-traumatic stress disorder or the normal on the basis of the brain activity data of the source activity in at least one area of cingulate gyms, fusiform gyrus, inferior occipital gyrus, inferior temporal gyms, lingual gyms, medial frontal gyrus, middle occipital gyrus, parahippocampal gyrus, posterior cingulate, sub-gyral, superior frontal gyms, and superior occipital gyms, as learning data.

According to another characteristic of the present invention, the classification model may be configured to classify the major depressive disorder or the normal. At this time, the classification model may be a model trained to classify the major depressive disorder or the normal on the basis of the brain activity data of the source activity in at least one brain area of angular gyrus, cuneus, fusiform gyrus, inferior occipital gyrus, lingual gyrus, parahippocampal gyrus, posterior cingulate, precuneus, and superior occipital gyrus, as learning data.

According to still another characteristic of the present invention, the classification model may be configured to classify the post-traumatic stress disorder or the major depressive disorder. At this time, the classification model may be a model trained to classify the post-traumatic stress disorder or the major depressive disorder on the basis of the brain activity data of the source activity in at least one brain area of cingulate gyrus, posterior cingulate, and sub-gyral, as learning data.

In the meantime, the classification model may be a model on the basis of at least one algorithm of a support vector machine (SVM), a decision tree, a random forest, adaptive boosting (AdaBoost), and penalized logistic regression (PLR). However, the classification model of the present invention is not limited thereto and may be provided on the basis of various learning algorithms.

Hereinafter, the device for provision of information on a mental disorder according to various exemplary embodiments of the present invention will be described in detail with reference to FIGS. 1A and 1B.

FIG. 1A is a schematic view for explaining a system for provision of information on a mental disorder using biosignal data according to an exemplary embodiment of the present invention. FIG. 1B is a schematic view for explaining a device for provision of information on a mental disorder according to an exemplary embodiment of the present invention.

First, referring to FIG. 1A, a system 1000 for provision of information on a mental disorder may be a system configured to provide information related to a mental disorder on the basis of a brain wave of a user according to auditory or visual stimulus. At this time, the system 1000 for provision of information on a mental disorder may include a device 100 for provision of information on a mental disorder configured to output a stimulus and determine whether a mental disorder is present in a subject, on the basis of brain wave data and brain activity data, a brain wave measuring device 200 configured to be in close contact with a scalp of a user to measure a brain wave, and a mobile device 300 of a user.

The device 100 for provision of information on a mental disorder is connected to be communicable with the brain wave measuring device 200 to acquire brain wave data and brain activity data of the user according to an output stimulus.

At this time, the brain measuring device 200 may be configured of a plurality of electrodes configured to enclose a head of the user from the outside. In the meantime, the plurality of electrodes may include at least two standard electrodes among Fp1, Fp2, F3, Fz, F4, F8, T7, C3, C4, Cz, T8, P7, P3, Pz, P4, P8, O1, O2, FCz, TP9, TP10, Oz, AFz, F7, Fpz, AF7, AF3, AF4, AFB, F9, F5, F1, F2, F6, F10, FT9, FT7, FC5, FC3, FC1, FC2, FC4, FC6, FT8, FT10, C5, C1, C2, C6, TP7, CP5, CP3, CP1, CPz, CP2, CP4, CP6, TP8, P9, P5, P1, P2, P6, P10, PO9, PO7, PO3, POz, PO4, PO8, PO10, O9, Iz, O10, F11, F12, FT11, FT12, TP11, TP12, PO11, PO12, P11, P12, I11, I12, and IIz.

Desirably, the brain wave measuring device 200 may be configured by at least Fz, Cz, Pz, T7, and T8 electrodes and to output electroencephalogram (EEG) measured at each channel, but is not limited thereto.

Figure 1B:
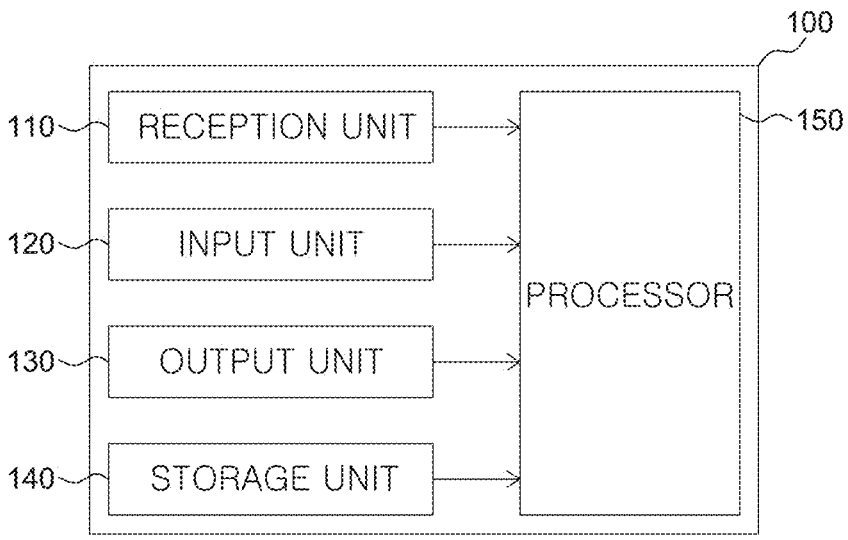
FIG. 1B is a schematic view for explaining a device for provision of information on a mental disorder according to an exemplary embodiment of the present invention.

In the meantime, referring to FIG. 1B together, the device 100 for provision of information on a mental disorder may include a reception unit 110, an input unit 120, an output unit 130, a storage unit 140, and a processor 150.

At this time, the reception unit 110 may be configured to receive brain wave signal data measured at each of a plurality of electrodes which forms the brain wave measuring device 200, for example, each of Fz, Cz, Pz, T7, and T8 electrodes. Moreover, according to various exemplary embodiments, the reception unit 110 may be further configured to receive brain activity data from a brain electromagnetic tomography (not illustrated).

The input unit 120 may be a keyboard, a mouse, or a touch screen panel, but is not limited thereto. The input unit 120 may set the device 100 for provision of information on a mental disorder and instruct an operation thereof. Moreover, when a standard sound stimulus and a target sound stimulus are output, the input unit 120 may be further configured to receive selection when the target sound stimulus is generated from the user.

The output unit 130 may be configured to output a visual stimulus or an auditory stimulus. Further, the output unit 130 may display brain wave data received by the reception unit 110. Moreover, the display unit 130 may display information on a mental disorder which is generated by the processor 150.

The storage unit 140 may be configured to store various brain wave data and brain activity data received by the reception unit 110, selections of the user input by means of the input unit 120, and contents associated with the stimulus provided by means of the output unit 130. Moreover, the storage unit 140 may be further configured to store information associated with the mental disorder which is classified or determined by the processor 150 to be described below. However, the storage unit is not limited thereto so that the storage unit 140 may be configured to store all data generated during a process of classifying mental disorders having a high incidence risk on the basis of a new brain wave signal by the processor 150.

The processor 150 may be provided on the basis of a classification model configured to predict the incidence of the mental disorder on the basis of the brain wave data acquired by means of the brain wave measuring device 200 and the brain activity data and to classify the mental disorder having a high incidence risk.

In the meantime, the processor 150 may be configured to generate brain wave activity data on the basis of the brain wave data.

According to the characteristic of the present invention, the processor 150 may be configured to determine brain activity data corresponding to a latency, with respect to brain activity data of a source activity for a brain area which is activated while the stimulus is output by the output unit 130.

According to another characteristic of the present invention, the processor 150 may be configured to convert the brain wave data into brain activity data using at least one of low-resolution brain electromagnetic tomography (LORETA), standardized low-resolution brain electromagnetic tomography (sLORETA), exact resolution brain electromagnetic tomography (eLORETA), minimum-norm estimate (MNE), dynamic statistical parametric mapping (dSPM), linearly constrained minimum variance (LCMV) beamformers programs—LORETA/sLORETA toolbox, Brainstrom, eConnectome, fieldtrip, and EEGlab.

According to still another characteristic of the present invention, the processor 150 may be on the basis of a classification model configured to classify at least one of a post-traumatic stress disorder, a major depressive disorder, a post-traumatic stress disorder having a major depressive disorder, and the normal. Accordingly, the device 100 for provision of information on a mental disorder according to the exemplary embodiment of the present invention may determine information associated with the mental disorder with a high accuracy.

Referring to FIG. 1 again, the device 100 for provision of information on a mental disorder may communicate with the mobile device 300 to provide information determined by the processor 150 to the mobile device 300.

Therefore, the user may easily acquire information on his/her own mental health without having temporal or spatial restrictions using the mobile device 300.

Figure 2:
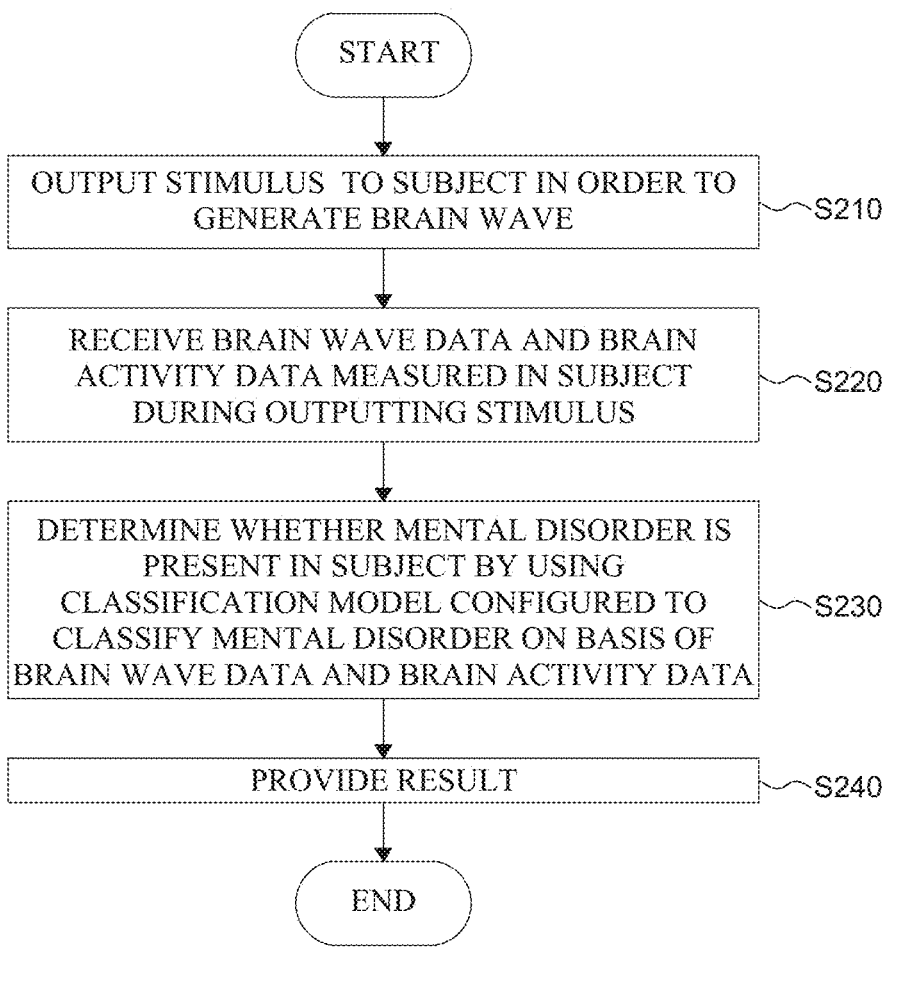
FIG. 2 is a schematic flowchart for explaining a method for determining whether a mental disorder occurs, on the basis of brain wave data and brain activity data of a subject in a device for provision of information on a mental disorder according to an exemplary embodiment of the present invention.

FIG. 2 is a schematic flowchart for explaining a method for determining whether a mental disorder occurs, on the basis of brain wave data and brain activity data of a user in a device for provision of information on a mental disorder according to an exemplary embodiment of the present invention.

First, according to the method for provision of information on a mental disorder according to the exemplary embodiment of the present invention, a stimulus is output to a subject in order to generate brain waves (S210). Next, brain wave data and brain activity data measured in a subject during outputting the stimulus are received (S220). Next, whether a mental disorder is present in the subject is determined by using a classification model configured to classify mental disorders on the basis of the brain wave data and the brain activity data (S230) and a final result is provided (S240).

According to the exemplary embodiment of the present invention, in the step (S210) of outputting a stimulus to a subject, visual and/or auditory stimulus inducing the generation of the brain wave or change of the brain wave may be output.

According to another exemplary embodiment of the present invention, in the step (S210) of outputting a stimulus to a subject, auditory stimuli configured by a standard sound stimulus of 1000 Hz and a target sound stimulus of 1500 Hz may be randomly output for the subject.

In the meantime, after the step (S210) of outputting a stimulus to a subject, a step of inputting the selection of the target sound stimulus by the subject may be further performed.

Next, in the step (S220) of receiving brain wave data and brain activity data, the brain wave data and the brain activity data measured in the subject during the outputting the stimulus may be received.

At this time, the brain wave data may include data of an amplitude or a latency.

According to another exemplary embodiment of the present invention, the amplitude data may include amplitude brain wave data in at least one standard electrode placement area of Fz, Cz, Pz, C3, T3 (T7), and T4 (T8) and the latency data may include brain wave data of the latency in at least one standard electrode placement area of Fz, Cz, Pz, C3, T3 (T7), and T4 (T8).

In the meantime, before the step (S220) of receiving brain wave data and brain activity data, a step of generating brain wave activity data on the basis of the brain wave data may be further performed.

To be more specific, in the step of generating brain wave activity data, brain activity data defined as a source activity for a brain area which is activated during generating the stimulus may be determined.

According to another exemplary embodiment of the present invention, the brain wave data includes latency data and in the step of generating brain wave activity data, a step of measuring brain activity data defined as a source activity for a brain area which is activated in a predetermined source space and a step of determining brain activity data corresponding to the latency may be performed during generating the stimulus.

According to still another exemplary embodiment of the present invention, the predetermined source space is a cortical gray matter and a plurality of latency data is provided. In the step of generating brain wave activity data, a step of determining brain activity data corresponding to the latency, on the basis of an average and a standard deviation for the plurality of latency data may be performed.

For example, in the step of generating brain wave activity data, a source space of the cortical gray matter of 6239 voxels having a resolution of 5 mm may be generated. Next, a time window may be set on the basis of the average and the standard deviation of the latency data. To be more specific, the time window may be a time obtained by adding or subtracting twice the standard deviation to or from the average P300 latency. Therefore, finally, brain activity data corresponding to the time window, for example, P300 brain activity data may be determined.

According to another exemplary embodiment of the present invention, in the step of generating brain wave activity data, the brain wave data may be converted into brain activity data by at least one of low-resolution brain electromagnetic tomography (LORETA), standardized low-resolution brain electromagnetic tomography (sLORETA), exact resolution brain electromagnetic tomography (eLORETA), minimum-norm estimate (MNE), dynamic statistical parametric mapping (dSPM), linearly constrained minimum variance (LCMV) beamformers programs—LORETA/sLORETA toolbox, Brainstrom, eConnectome, fieldtrip, and EEGlab.

However, the brain activity data is not limited thereto.

For example, in the step (S220) of receiving brain wave data and brain activity data, the brain activity data including a source activity in at least one brain area of anterior cingulate, cingulate gyms, cuneus, fusiform gyms, inferior occipital gyms, inferior temporal gyms, insula, lingual gyrus, medial frontal gyrus, middle frontal gyms, middle occipital gyms, middle temporal gyrus, parahippocampal gyms, posterior cingulate, precuneus, sub-gyral, superior frontal gyms, superior occipital gyrus, superior temporal gyrus, transverse temporal gyms, uncus, angular gyrus, and inferior frontal gyrus may be received.

According to still another exemplary embodiment of the present invention, after the step (S220) of receiving brain wave data and brain activity data, brain wave data having a maximum value generated between 200 and 500 ms may be determined after inputting selection for a target sound stimulus to the subject.

Next, it is determined whether the mental disorder is present in the subject by the classification model configured to classify mental disorders on the basis of the brain wave data and the brain activity data.

In the step (S230) of determining whether the mental disorder is present in the subject, the classification model may be a model configured to classify at least one of a post-traumatic stress disorder, a major depressive disorder, a post-traumatic stress disorder having a major depressive disorder, and the normal, on the basis of the brain wave data and the brain activity data.

In the meantime, according to still another exemplary embodiment of the present invention, different brain activity data may be used depending on a type of a target disease to be classified by the classification model.

For example, the classification model may be a model trained to classify the post-traumatic stress disorder or the normal on the basis of the brain activity data of the source activity in at least one area of cingulate gyms, fusiform gyrus, inferior occipital gyrus, inferior temporal gyms, lingual gyms, medial frontal gyrus, middle occipital gyrus, parahippocampal gyrus, posterior cingulate, sub-gyral, superior frontal gyms, and superior occipital gyms, as learning data.

Further, the classification model may be a model trained to classify the major depressive disorder or the normal on the basis of the brain activity data of the source activity in at least one brain area of angular gyrus, cuneus, fusiform gyrus, inferior occipital gyrus, lingual gyrus, parahippocampal gyrus, posterior cingulate, precuneus, and superior occipital gyrus, as learning data.

Moreover, the classification model may be a model trained to classify the post-traumatic stress disorder or the major depressive disorder on the basis of the brain activity data of the source activity in at least one brain area of cingulate gyrus, posterior cingulate, and sub-gyral, as learning data.

As a result of the step (S230) of determining whether a mental disorder is present in the subject, information associated with the mental disorder for the subject may be determined and finally, in the step (S240) of providing a result, various information determined by the classification model may be output or transmitted to the mobile device of the user.

As described above, the method for provision of information on a mental disorder according to various exemplary embodiments of the present invention may allow a user to easily acquire information on a mental health of the user without having temporal and spatial restrictions.

Hereinafter, an evaluation result of a device for provision of information on a mental disorder according to an exemplary embodiment of the present invention will be described with reference to FIGS. 3, 4A to 4C, 5A to 5E, 6A, 6B, and 7.

In the meantime, for this evaluation, as brain wave data, an amplitude and a latency of p300 have been used and as brain activity data, p300 source activity has been used, but are not limited thereto.

FIG. 3 illustrates evaluation data of a device for provision of information on a mental disorder according to an exemplary embodiment of the present invention.

Referring to FIG. 3, data for a total of 51 subjects having a post-traumatic stress disorder (PTSD), 67 subjects having a major depressive disorder (MDD), and 39 healthy subjects of a control group (HCs) were used for this evaluation.

At this time, the subjects having a post-traumatic stress disorder (PTSD) were configured by 28 subjects having only the post-traumatic stress disorder (PTSD-mono diagnosis, PTSDm) and 23 subjects having the post-traumatic stress disorder accompanied by depression (PTSD-comorbid diagnosis, PTSDc).

To be more specific, an average score of beck anxiety inventory (BAI) of the subjects (PTSDc) having the post-traumatic stress disorder accompanied by the depression was 31.38 which was higher than an average score of 28.71 of the subjects (PTSDm) having only the post-traumatic stress disorder.

Further, an average score of impact of event scale-revises (IES-R) of the subjects (PTSDc) having the post-traumatic stress disorder accompanied by the depression was 55.00 which was higher than an average score of 53.38 of the subjects (PTSDm) having only the post-traumatic stress disorder.

In the meantime, the average BDI (beck depression inventory) score of the subjects (MDD) having a major depressive disorder was 25.81.

Various evaluations were performed on the basis of data of the subjects having the clinical characteristics as described above.

Figure 4A:
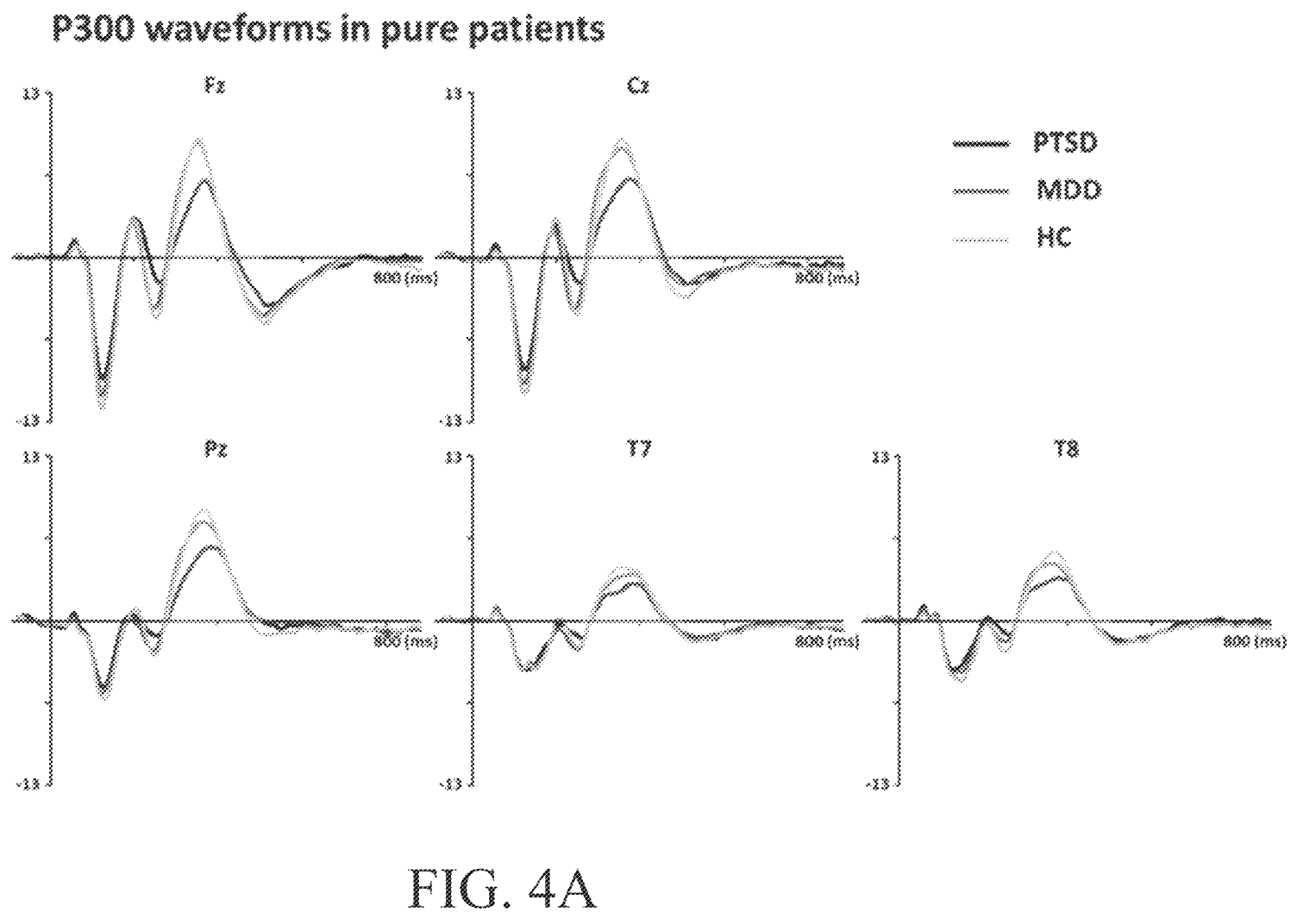
Figure 4B:
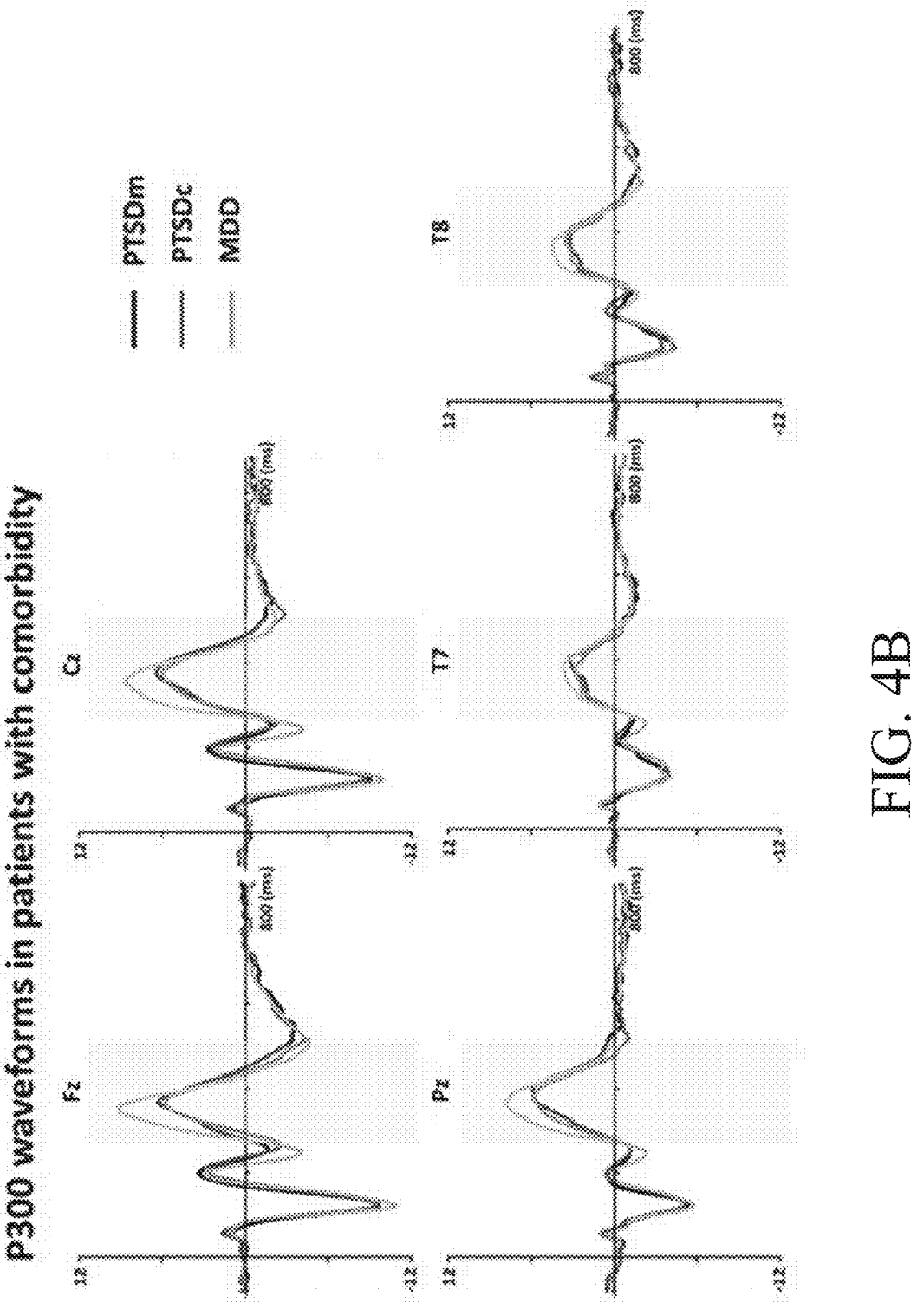

First Evaluation: Classification Performance Evaluation (Brain Wave Data) of a Device for Extraction of a Feature for Classification of Mental Disorders and Provision of Information on a Mental Disorder FIGS. 4A to 4C illustrate a brain wave data analysis result on whether a mental disorder is present in a subject.

Referring to FIG. 4A, p300 amplitude measured from Fz, Cz, Pz, T7, and T8 electrodes for subjects having a post-traumatic stress disorder (PTSD), subjectshaving a major depressive disorder (MDD), and healthy subjects in a control group (HC) is illustrated.

To be more specific, it is illustrated that the subjects having a post-traumatic stress disorder (PTSD) and the subjects having a major depressive disorder (MDD) have a lower signal value than the healthy subjects (HC), in all the electrodes of Fz, Cz, Pz, T7, and T8.

Specifically, it is illustrated that the subjects having a post-traumatic stress disorder (PTSD) has a lower signal value than the subjects having a major depressive disorder (MDD) in the p300 amplitude.

Referring to FIG. 4B, p300 amplitude measured from Fz, Cz, Pz, T7, and T8 electrodes for the subjects having the post-traumatic stress disorder accompanied by the depression (PTSDc), the subjects having only the post-traumatic stress disorder (PTSDm), and the subjects having a major depressive disorder (MDD) is illustrated. To be more specific, it is illustrated that the subjects having the post-traumatic stress disorder accompanied by the depression (PTSDc) and the subjects having only the post-traumatic stress disorder (PTSDm) have a lower signal value than the subjects having a major depressive disorder (MDD) in the p300 amplitude.

Referring to FIG. 4C together, signal values of p300 amplitude and p300 latency measured from Fz, Cz, Pz, T7, and T8 electrodes for the subjects having a post-traumatic stress disorder (PTSD), the subjects having a major depressive disorder (MDD), and the healthy subjects in the control group (HC) are illustrated.

To be more specific, signal values for p300 amplitude and p300 latency for subjects of three groups have statistically significant differences.

Figure 5A:
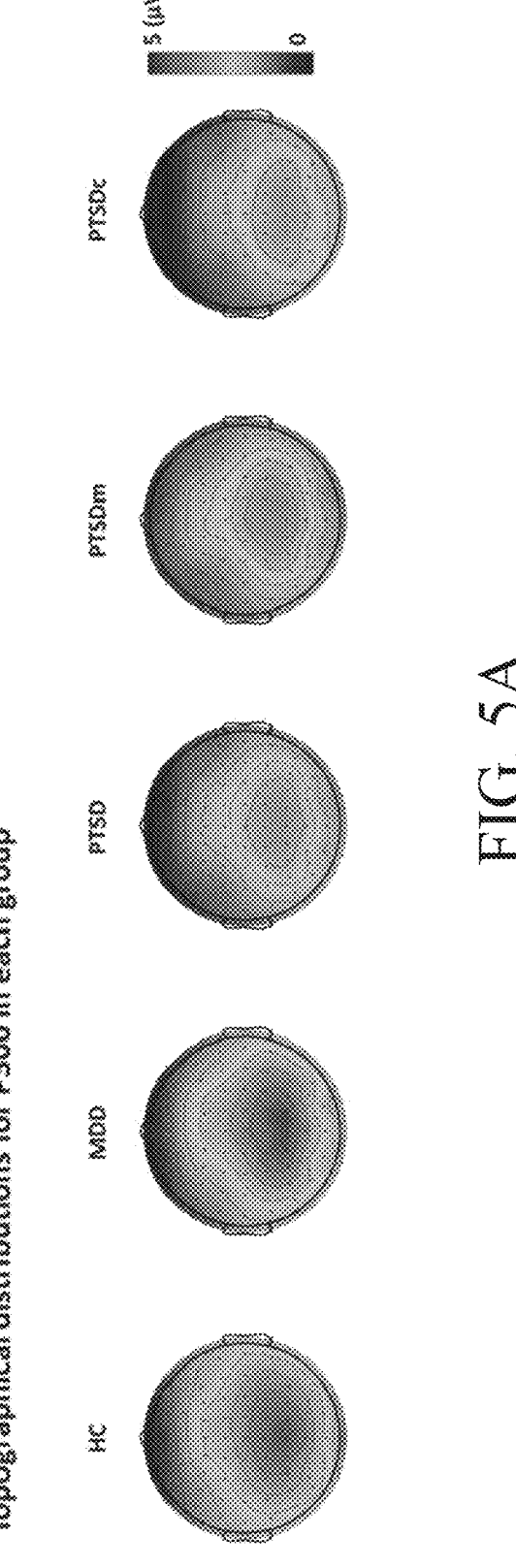

Further referring to FIG. 5A, topographical distributions of an average p300 ERP component for the healthy subjects in the control group (HC), the subjects having a major depressive disorder (MDD), the subjects having a post-traumatic stress disorder (PTSD), the subjects having only the post-traumatic stress disorder (PTSDm), and the subjects having the post-traumatic stress disorder accompanied by the depression (PTSDc) are illustrated.

To be more specific, topographical distributions for subjects of three groups of the healthy subjects in the control group (HC), the subjects having a major depressive disorder (MDD), and the subjects having a post-traumatic stress disorder (PTSD) have statistically significant differences.

Accordingly, the p300 brain wave data, specifically, the brain wave data such as p300 amplitude and p300 latency measured from Fz, Cz, Pz, T7, and T8 electrodes may be used as feature data for classifying the post-traumatic stress disorder, the major depressive disorder, or the normal.

Specifically, the brain wave data may be applied to classify diseases which share the similar symptoms, such as the post-traumatic stress disorder and the major depressive disorder.

Second Evaluation: Classification Performance Evaluation (Brain Activity Data) of a Device for Extraction of Feature for Classification of Mental Disorders and Provision of Information on a Mental Disorder At this time, as the brain activity data, a source activity for a brain area acquired by sRORETA was used, but is not limited thereto.

FIGS. 5A to 5D illustrate a brain activity data analysis result depending on whether a mental disorder is present in a subject.

Referring to FIG. 5A, in two groups, a brain area in which p300 source activity shows a significant difference is illustrated.

To be more specific, it is illustrated that a source activity of the subject having a post-traumatic stress disorder (PTSD) is significantly reduced as compared with the healthy subject in the control group (HC) in anterior cingulate, cingulate gyrus, cuneus, fusiform gyrus, inferior occipital gyms, inferior temporal gyrus, insula, lingual gyrus, medial frontal gyms, middle occipital gyrus, parahippocampal gyms, posterior cingulate, precuneus, sub-gyral, superior temporal gyms, and uncus.

Referring to FIG. 5B together, cingulate gyms, fusiform gyms, inferior occipital gyrus, inferior temporal gyms, lingual gyms, medial frontal gyrus, middle occipital gyrus, parahippocampal gyrus, posterior cingulate, sub-gyral, superior frontal gyrus, and superior occipital gyms which are the brain areas in the subject having a post-traumatic stress disorder (PTSD) in which the source activity is significantly reduced as compared with the healthy control (HC) are blue.

This result means that the brain activity data of cingulate gyrus, fusiform gyrus, inferior occipital gyrus, inferior temporal gyms, lingual gyrus, medial frontal gyrus, middle occipital gyms, parahippocampal gyms, posterior cingulate, sub-gyral, superior frontal gyrus, and superior occipital gyrus can be used as feature data for determining whether the post-traumatic stress disorder occurs.

Referring to FIG. 5A again, it is illustrated that the source activity of the subject having a major depressive disorder (MDD) is significantly reduced in cuneus, fusiform gyms, lingual gyms, parahippocampal gyms, and posterior cingulate as compared with the healthy control (HC).

Figure 5C:
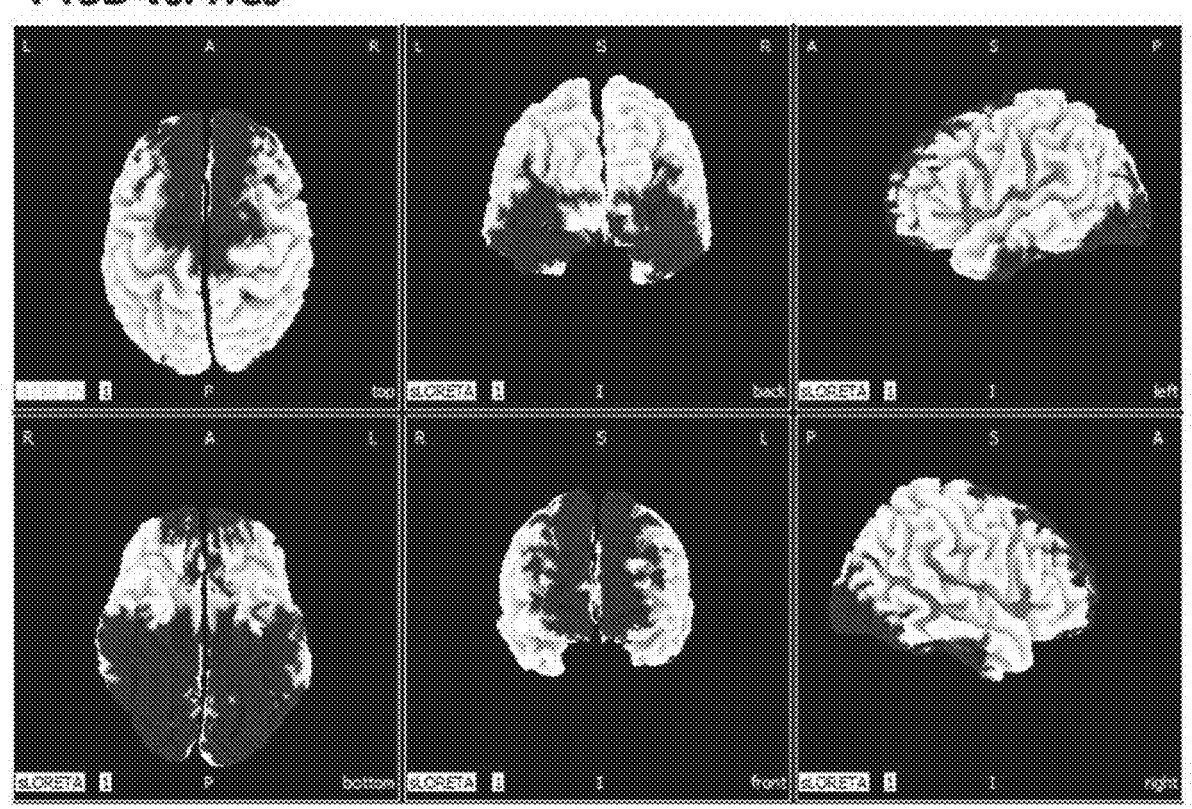

At this time, referring to FIG. 5C together, angular gyrus, cuneus, fusiform gyrus, inferior frontal gyms, lingual gyrus, parahippocampal gyrus, posterior cingulate, precuneus, and superior occipital gyrus which are the brain areas in the subject having a major depressive disorder (MDD) in which the source activity is significantly reduced as compared with the healthy control (HC) are blue.

This result means that the brain activity data of angular gyms, cuneus, fusiform gyrus, inferior frontal gyms, lingual gyrus, parahippocampal gyrus, posterior cingulate, precuneus, and superior occipital gyrus can be used as feature data for determining whether the major depressive disorder occurs.

Referring to FIG. 5A again, it is illustrated that the source activity of the subject having a post-traumatic stress disorder (PTSD) is significantly reduced in angular gyrus, anterior cingulate, cingulate gyrus, cuneus, insula, medial frontal gyrus, middle frontal gyrus, middle temporal gyrus, parahippocampal gyrus, posterior cingulate, precuneus, sub-gyral, superior frontal gyms, superior occipital gyms, superior temporal gyrus, and transverse temporal gyms as compared with the subject having a major depressive disorder (MDD).

Specifically, it is illustrated that the source activity of the subject having a post-traumatic stress disorder accompanied by the depression (PTSDc) is significantly reduced as compared with the subject having a major depressive disorder (MDD) in anterior cingulate, cingulate gyrus, inferior frontal gyrus, medial frontal gyms, and superior temporal gyrus.

Figure 5D:
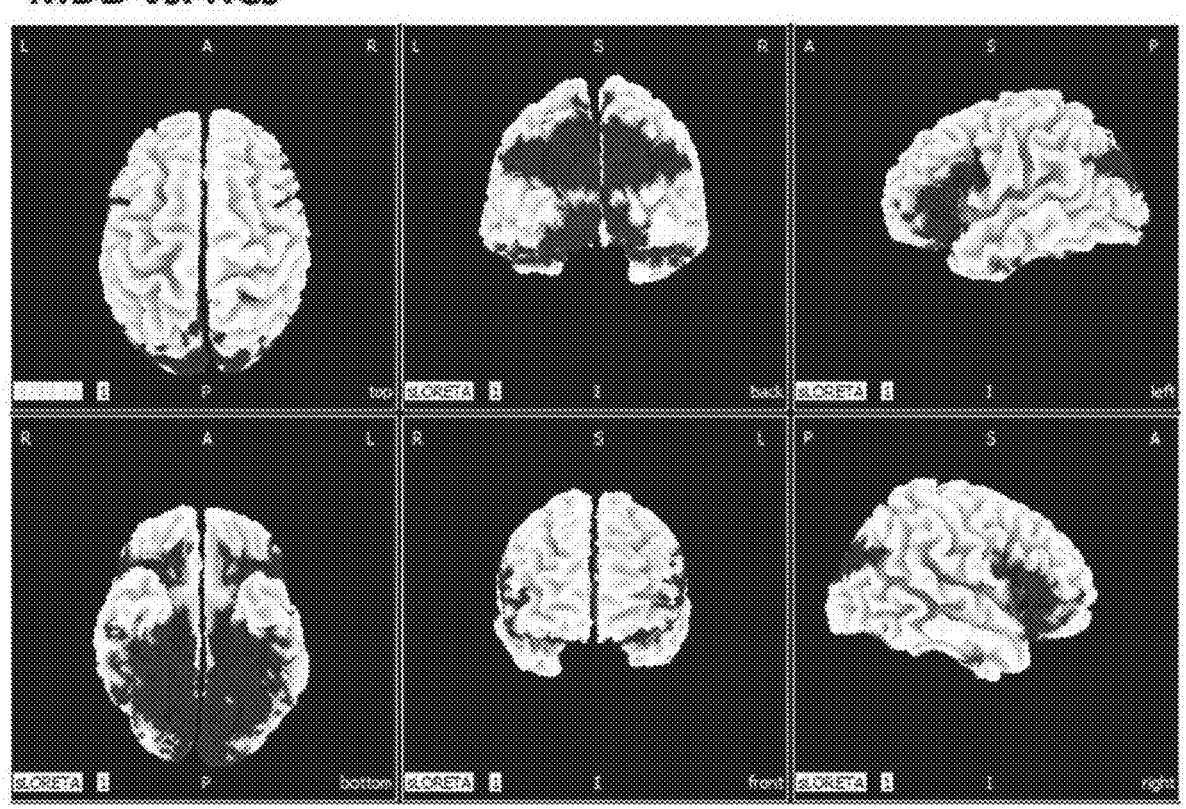
Figure 5E:
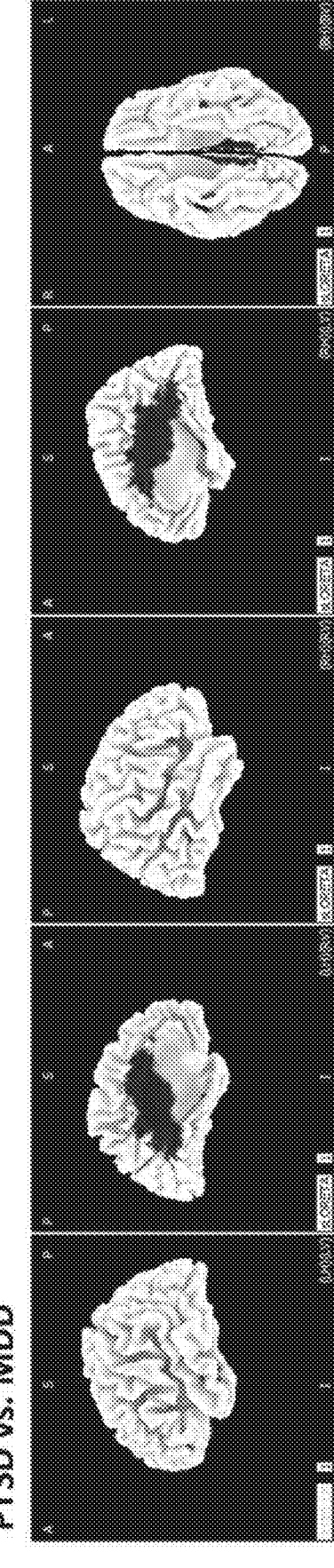

At this time, referring to FIG. 5D together, cingulate gyrus, posterior cingulate, and sub-gyral which are brain areas in the subject having a post-traumatic stress disorder in which the source activity is significantly reduced as compared with the subject having a major depressive disorder (MDD) are blue.

That is, this result means that the brain activity data of cingulate gyrus, posterior cingulate, and sub-gyral can be used as a feature for classifying diseases which share the similar symptoms of the major depressive disorder and the post-traumatic stress disorder.

Accordingly, the device for provision of information according to the exemplary embodiment of the present invention may provide information with a high reliability on the basis of a combination of brain activity data which is set to be different by determining whether the post-traumatic stress disorder occurs and whether the major depressive disorder occurs or classifying two mental disorders.

Specifically, when the classification model is applied, different brain activity data according to a learning goal may be applied so as to increase the accuracy of the classification.

Third Evaluation: Classification Performance Evaluation of a Device for Provision of Information on a Mental Disorder (Brain Wave Data and Brain Activity Data)

Figure 6A:
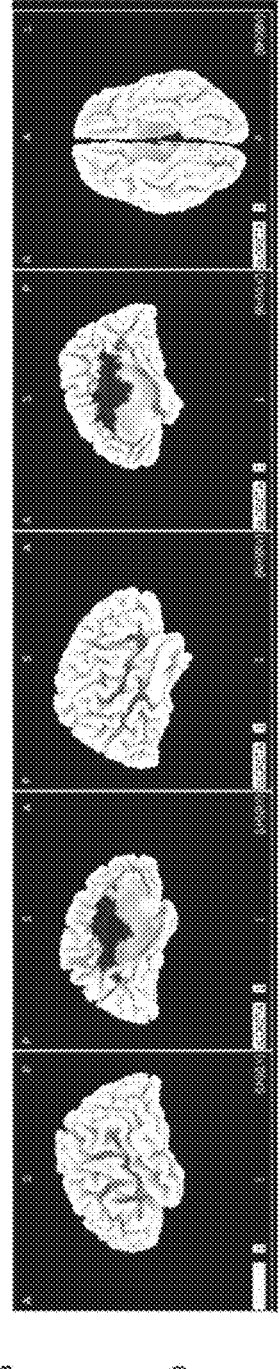
FIGS. 6A and 6B illustrate analysis results of brain wave data and brain activity data according to a type of mental disorder of a subject.
Figure 6A:
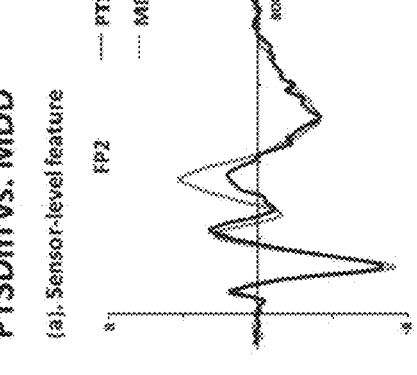
Figure 6B:
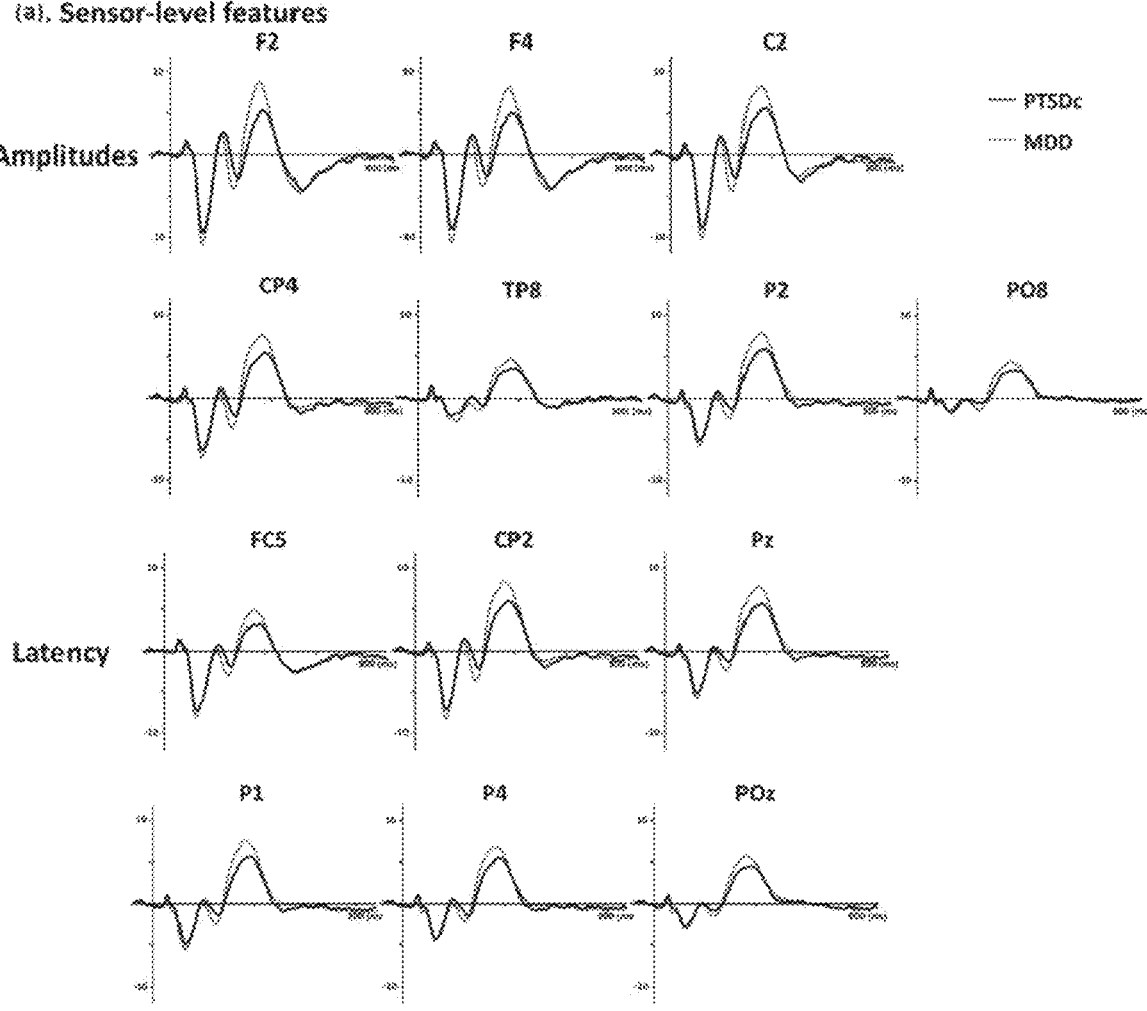
Figure 6B:
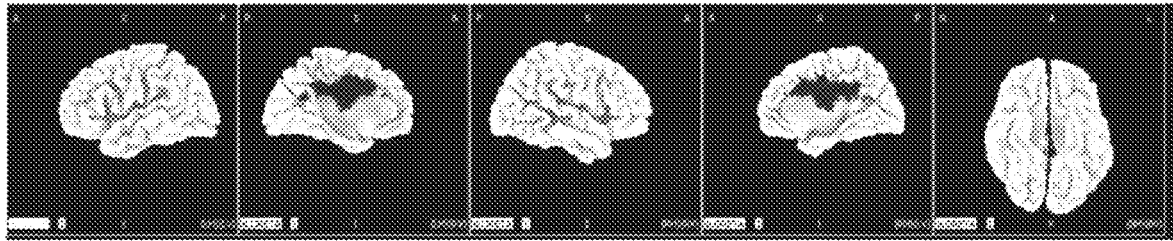

FIGS. 6A and 6B illustrate analysis results of brain wave data and brain activity data according to a type of the onset mental disorder of a subject.

Referring to FIG. 6A(a), in the case of the subject having only the post-traumatic stress disorder (PTSDm), a level of p300 amplitude in FP2 electrode is significantly low as compared with the subject having a major depressive disorder (MDD).

Referring to FIG. 6A(b), in the case of the subject having only the post-traumatic stress disorder (PTSDm), the source activity in cingulate gyrus is reduced as compared with the subject having a major depressive disorder (MDD).

This result means that the brain wave data such as p300 amplitude in FP2 electrode and the brain activity data such as a source activity of cingulate gyrus can be used to classify only the post-traumatic stress disorder or the major depressive disorder.

Referring to FIG. 6B(a), in the case of the subject having the post-traumatic stress disorder accompanied with the depression (PTSDc), a level of p300 amplitude in F2, F4, C2, CP4, TP8, P2, and PO8 electrodes is significantly low as compared with the subject having a major depressive disorder (MDD). Moreover, the level of p300 latency in FC5, CP2, Pz, P1, P4, and POz electrodes is significantly low.

Referring to FIG. 6B(b), in the case of the subject having the post-traumatic stress disorder accompanied by the depression (PTSDc), the source activity in cingulate gyms is reduced as compared with the subject having a major depressive disorder (MDD).

This result means that the brain wave data such as p300 amplitude in F2, C2, CP4, TP8, P2, and PO8 electrodes and p300 latency in FC5, CP2, Pz, P1, P4, and POz electrodes and the brain activity data such as a source activity of cingulate gyms can be used to classify the post-traumatic stress disorder accompanied by the depression or the major depressive disorder.

Fourth Evaluation: Performance Evaluation of Classification Model

FIG. 7 illustrates a mental disorder classification result on the basis of a classification model used for various exemplary embodiments of the present invention.

Referring to FIG. 7, a result of classifying seven classification pairs using a classification model on the basis of brain wave signal data corresponding to a sensor value (sensor) or brain activity data corresponding to a source activity (source), or two data (sensor+source) is illustrated.

At this time, the seven classification pairs may include 1) a subject having a major depressive disorder (MDD) or a healthy subject of a control group (HCs), 2) a subject having a post-traumatic stress disorder (PTSD) or a healthy subject of a control group (HCs), 3) a subject having a post-traumatic stress disorder (PTSD) or a subject having a major depressive disorder (MDD), 4) a subject having only a post-traumatic stress disorder (PTSDm) or a healthy subject of a control group (HCs), 5) a subject having only a post-traumatic stress disorder (PTSDm) or a subject having a major depressive disorder (MDD), 6) a subject having a post-traumatic stress disorder accompanied by the depression (PTSDc) or a healthy subject of a control group (HCs), and 7) a subject having a post-traumatic stress disorder accompanied by the depression (PTSDc) or a subject having a major depressive disorder (MDD).

To be more specific, referring to the classification result of the classification model for the subject having a major depressive disorder (MDD) or the healthy subject of a control group (HCs), the accuracy on the basis of the brain activity data (source) is 67.92% which is the highest. Moreover, referring to the classification result of the classification model for the subject having a post-traumatic stress disorder (PTSD) or the healthy subject of a control group (HCs), the accuracy on the basis of the brain activity data (source) is 80.00% which is the highest. Moreover, referring to the classification result of the classification model for the subject having a post-traumatic stress disorder (PTSD) or the subject having a major depressive disorder (MDD), the accuracy on the basis of the brain activity data (source) is 70.34% which is the highest. Moreover, referring to the classification result of the classification model for the subject having only the post-traumatic stress disorder (PTSDm) or the healthy subject of a control group (HCs), the accuracy on the basis of the brain activity data (source) is 82.09% which is the highest. Further, referring to the classification result of the classification model for the subject having a post-traumatic stress disorder accompanied by the depression (PTSDc) or the healthy subject of a control group (HCs), the accuracy on the basis of the brain activity data (source) is 82.26% which is the highest.

In the meantime, referring to the classification result of the classification model for the subject having only a post-traumatic stress disorder (PTSDm) or the subject having a major depressive disorder (MDD), the accuracy on the basis of the brain wave data and the brain activity data (sensor+source) is 71.58% which is the highest. Further, referring to the classification result of the classification model for the subject having a post-traumatic stress disorder accompanied by the depression (PTSDc) or the subject having a major depressive disorder (MDD), the accuracy on the basis of the brain wave data and the brain activity data (sensor+source) is 76.67% which is the highest.

That is, when not only the brain activity data, but also both the brain wave data and the brain activity data are used, the classification model may classify the onset mental disorder with a high accuracy.

Therefore, the classification model may predict whether the major depressive disorder or the post-traumatic stress disorder occurs, on the basis of the brain activity data, and further two data of the brain wave data and the brain activity data with a high reliability. Further, the classification model may classify two diseases which share the similar symptoms such as the major depressive disorder and the post-traumatic stress disorder (sole or accompanied by the depression) with a high accuracy.

Accordingly, the device for provision of information according to the exemplary embodiment may provide various information predicted by the classification model as information for mental disorder having a high reliability.

Specifically, the device for provision of information according to the exemplary embodiment may classify two similar diseases such as the post-traumatic stress disorder accompanied by the depression and the major depressive disorder and provide the classification result as diagnostic information for the mental disorder.

That is, according to the present invention, not only brain wave data according to the specific stimulus which may be acquired from a sensor of the brain wave signal, but also the application of brain activity data of a source activity which is activated while outputting the stimulus can contribute to the accurate diagnosis of the mental disorder.

Therefore, the present invention may overcome the limitations of the analysis method such as fMRI having many limitations that focus only on the neural activity during the processing of emotional information, but do not consider important pathologies such as an altered cognitive process so that information with a low reliability is provided and has many limitations such as accompanied expensive analysis costs and spatial and temporal restrictions.

Although the exemplary embodiments of the present invention have been described in detail with reference to the accompanying drawings, the present invention is not limited thereto and may be embodied in many different forms without departing from the technical concept of the present invention. Therefore, the exemplary embodiments of the present invention are provided for illustrative purposes only but not intended to limit the technical concept of the present invention. The scope of the technical concept of the present invention is not limited thereto. Therefore, it should be understood that the above-described exemplary embodiments are illustrative in all aspects and do not limit the present invention. The protective scope of the present invention should be construed based on the following claims, and all the technical concepts in the equivalent scope thereof should be construed as falling within the scope of the present invention.

100: Device for provision of information on mental disorder
    110: Reception unit
    120: Input unit
    130: Output unit
    140: Storage unit
    150: Processor 200: Brain wave measuring device
300: Mobile device
1000: System for provision of information on mental
disorder

NATIONAL R&D PROJECT SUPPORTING THIS INVENTION

[Project ID number] 201802750002, [Government department name] National Research Foundation of Korea, [Research management institution] Inje University Industry-Academic Cooperation Foundation, [Research project name] Source technology development project (Brain science source technology development project), [Research task name] EEG Biomarker development for prediction, early diagnosis, and therapeutic responsiveness evaluation of Post-traumatic stress disorder (Hosted by Ewha Womans University), [Contribution rate] 1/2, [Host organization] Inje University Industry-Academic Cooperation Foundation, [Research period] 20190201~20191231,

[Project ID number] 201802760002, [Government department name] National Research Foundation of Korea, [Research management institution] Inje University Industry-Academic Cooperation Foundation, [Research project name] Mid-career researcher program, [Research task name] Development of Prediction and Diagnostic tool for Mental Illness using EGG, Heart rate variability, and machine learning, [Contribution rate] 1/2, [Host organization] Inje University Industry-Academic Cooperation Foundation, [Research period] 20190301~20200229

What is claimed is:

1. A method for provision of information on a mental disorder being implemented by a processor, the method comprising: outputting a stimulus to a subject in order to generate brain waves, by randomly outputting to the subject a standard sound stimulus and target sound stimuli, the target sound stimuli including a target sound stimulus having a frequency that is different from the standard sound stimulus and a second target sound stimulus having a decibel level that is different from the standard sound stimulus; receiving from the subject a selection of one of the target sound stimuli randomly outputted to the subject receiving brain wave data and brain activity data measured in the subject during the outputting the stimulus; determining, among the received brain wave data, brain wave data having a maximum generated between 200 and 500 ms, the brain wave data determined based on the selected one of the target sound stimuli: and determining whether a mental disorder is present in the subject by using a classification model configured to classify mental disorders based on the brain wave data and the brain activity data.

2. The method of claim 1, further comprising:
generating the brain activity data based on the brain wave data.

3. The method of claim 2,
wherein the brain wave data includes latency data, and
wherein the generating the brain activity data includes:
measuring brain activity data defined as a source activity for a brain area which is activated in a predetermined source space during generating the stimulus; and
determining brain activity data corresponding to a latency of the latency data.

4. The method of claim 3,
wherein the predetermined source space is cortical gray matter,
wherein a plurality of latency data is provided, and
wherein the brain activity data corresponding to a latency of the latency data is determined based on an average and a standard deviation for the plurality of latency data.

5. The method of claim 2, wherein the generating the brain activity data includes:
converting the brain wave data into the brain activity data using at least one of low-resolution brain electromagnetic tomography (LORETA), standardized low-resolution brain electromagnetic tomography (sLORETA), exact resolution brain electromagnetic tomography (eLORETA), minimum-norm estimate (MNE), dynamic statistical parametric mapping (dSPM), linearly constrained minimum variance (LCMV) beamformers programs-LORETA/sLORETA toolbox, Brainstrom, eConnectome, fieldtrip, and EEGlab.

6. The method of claim 1, wherein the brain wave data includes amplitude data or latency data.

7. The method of claim 6, wherein the amplitude data includes amplitude data in at least one standard electrode placement area of Fz, Cz, Pz, C3, T3, T4, T7, and T8 and the latency data includes latency data in the at least one standard electrode placement area.

8. The method of claim 7, wherein the at least one standard electrode placement area consists of the Fz, the Cz, and the Pz.

9. The method of claim 1, wherein the brain activity data includes a source activity in at least one brain area of anterior cingulate, cingulate gyrus, cuneus, fusiform gyrus, inferior occipital gyrus, inferior temporal gyrus, insula, lingual gyrus, medial frontal gyrus, middle frontal gyrus, middle occipital gyrus, middle temporal gyrus, parahippocampal gyrus, posterior cingulate, precuneus, sub-gyral, superior frontal gyrus, superior occipital gyrus, superior temporal gyrus, transverse temporal gyrus, uncus, angular gyrus, and inferior frontal gyrus.

10. The method of claim 1, wherein the classification model is configured to classify at least one of a post-traumatic stress disorder, a major depressive disorder, a post-traumatic stress disorder having the major depressive disorder, and a healthy state of a normal subject, based on the brain wave data and the brain activity data.

11. The method of claim 10,
wherein the classification model is further configured to classify the post-traumatic stress disorder and the healthy state, and
wherein the brain activity data includes a source activity in at least one area of cingulate gyrus, fusiform gyrus, inferior occipital gyrus, inferior temporal gyrus, lingual gyrus, medial frontal gyrus, middle occipital gyrus, parahippocampal gyrus, posterior cingulate, sub-gyral, superior frontal gyrus, and superior occipital gyrus.

12. The method of claim 10,
wherein the classification model is further configured to classify the major depressive disorder and the healthy state, and
wherein the brain activity data includes a source activity in at least one brain area of angular gyrus, cuneus, fusiform gyrus, inferior occipital gyrus, lingual gyrus, parahippocampal gyrus, posterior cingulate, precuneus, and superior occipital gyrus.

13. The method of claim 10,
wherein the classification model is further configured to classify the post-traumatic stress disorder and the major depressive disorder, and
wherein the brain activity data includes a source activity in at least one brain area of cingulate gyrus, posterior cingulate, and sub-gyral.

14. A device for provision of information on a mental disorder, the device comprising: an audiovisual device configured to output a stimulus to a subject in order to generate brain waves, by randomly outputting to the subject a standard sound stimulus and target sound stimuli, the target sound stimuli including a target sound stimulus having a frequency that is different from the standard sound stimulus and a second target sound stimulus having a decibel level that is different from the standard sound stimulus; a user interface configured to receive from the subject a selection of one of the target sound stimuli randomly outputted to the subject; a plurality of electrodes configured to receive brain wave data and brain activity data measured in the subject during the outputting the stimulus; and a processor connected to communicate with the plurality of electrodes, wherein the processor is configured to determine, among the received brain wave data, brain wave data having a maximum generated between 200 and 500 ms, the brain wave data determined based on the selected one of the target sound stimuli; and determine whether a mental disorder is present in the subject by using a classification model configured to classify mental disorders based on the brain wave data and the brain activity data.

15. The device of claim 14, wherein the processor is further configured to generate the brain activity data based on the brain wave data.

16. The device of claim 15, wherein the brain wave data includes latency data, wherein the plurality of electrodes are further configured to receive brain activity data defined as a source activity for a brain area which is activated during generating the stimulus, and the processor is further configured to determine brain activity data corresponding to a latency of the latency data.

17. The device of claim 15, wherein the processor is further configured to convert the brain wave data into the brain activity data using at least one of low-resolution brain electromagnetic tomography (LORETA), standardized low-resolution brain electromagnetic tomography (sLORETA), exact resolution brain electromagnetic tomography (eLORETA), minimum-norm estimate (MNE), dynamic statistical parametric mapping (dSPM), linearly constrained minimum variance (LCMV) beamformers programs-LORETA/sLORETA toolbox, Brainstrom, eConnectome, fieldtrip, and EEGlab.

18. The device of claim 14, wherein the brain wave data includes amplitude data or latency data.

19. The device of claim 18, wherein the amplitude data includes amplitude data of the brain wave data received from only three standard electrode placement areas, the three standard electrode placement areas consisting of Fz, Cz, and Pz, and wherein the latency data includes latency data in the three standard electrode placement areas.

* * * * *